United States Patent [19]

Witiak et al.

[11] 4,393,226
[45] Jul. 12, 1983

[54] COMPOUNDS AND METHODS FOR CHANGING CALCIUM METABOLISM WITHIN THE CELLS OF A MAMMAL

[75] Inventors: Donald T. Witiak, Mount Vernon; Ralf G. Rahwan, Columbus, both of Ohio

[73] Assignee: The Ohio State University Research Foundation, Columbus, Ohio

[21] Appl. No.: 261,008

[22] Filed: May 6, 1981

[51] Int. Cl.³ .................... C07D 317/44; A61K 31/36
[52] U.S. Cl. ..................................... 549/433; 424/282
[58] Field of Search ................... 260/340.5 R; 549/433

[56] References Cited

U.S. PATENT DOCUMENTS

| | | | |
|---|---|---|---|
| 2,541,967 | 2/1951 | Kolloff et al. | 260/340.5 R |
| 2,916,490 | 12/1959 | Schenck et al. | 260/326.8 |
| 3,201,470 | 8/1965 | Huebner | 260/501.1 |
| 3,253,037 | 5/1966 | Huebner | 260/340.5 R |

OTHER PUBLICATIONS

D. T. Witiak, D. R. Williams, S. V. Kakodkar, C. Hite and M. S. Chen, *J. Org. Chem.*, 39, 1242 (1974).
R. G. Rahwan, M. M. Faust and D. T. Witiak, *J. Pharmacol. Exp. Ther.*, 201, 126 (1977).
M. F. Piascik, R. G. Rahwan and D. T. Witiak, *J. Pharmacol. Exp. Ther.*, 205, 155 (1978).
D. T. Witiak, S. V. Kakodkar, T. P. Johnson, J. R. Baldwin and R. G. Rahwan, *J. Med. Chem.*, 22, 77 (1979).
C. E. Akesson, R. G. Rahwan, D. T. Witiak, R. J. Brumbaugh, *Res. Commun. Chem. Pathol., Pharmacol.*, 27, 265, (1980).
R. G. Rahwan, M. F. Piascik, D. T. Witiak, *Canad. J. Physiol. Pharmacol.*, 57, 443, (1979).
M. F. Piascik, R. G. Rahwan and D. T. Witiak, *J. Pharmacol. Exp. Ther.*, 210, 141 (1979).
M. F. Piascik, M. T. Piascik, D. T. Witiak and R. G. Rahwan, *Canad. J. Physiol. Pharmacol.*, 57, 1350 (1979).
R. G. Rahwan, C. E. Akesson and D. T. Witiak, *Res. Common. Chem. Pathol. Pharmacol.*, 26, 85 (1979).
J. L. Lynch, R. G. Rahwan, and D. T. Witiak, *J. Card. Pharmcol.*, 60, 49 (1981).

*Primary Examiner*—Ethel G. Love
*Attorney, Agent, or Firm*—Millard & Cox

[57] ABSTRACT

2-alkyl-5,6-dialkoxy (or 5,6 alkylenedioxy) indenes and indane-1-di- or trialkylammonium salts are useful as calcium antagonists, for example in arrhythmia. The compounds are prepared from the known corresponding 2,5,6-substituted indene-1-dimethylammonium salts by alkylation and/or hydrogenation.

30 Claims, 1 Drawing Figure

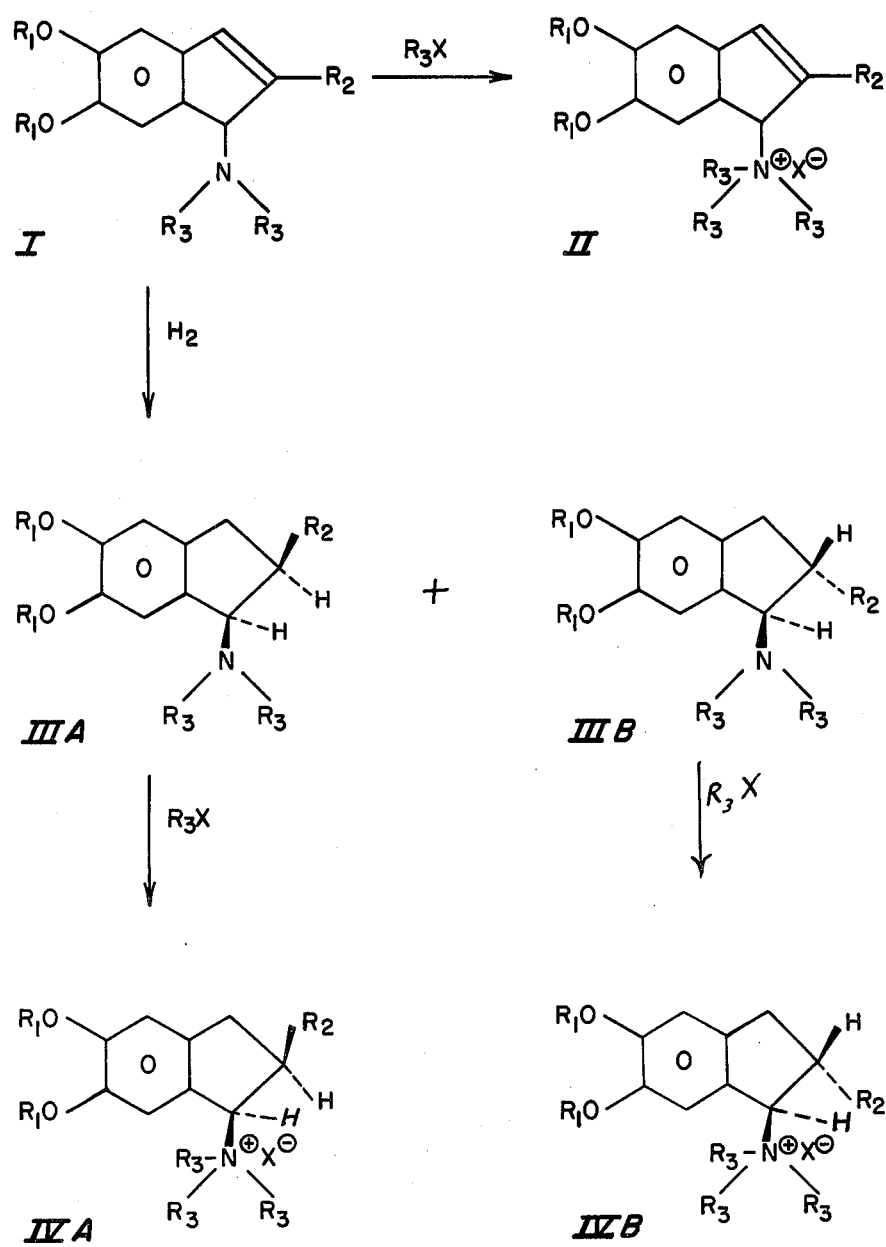

COMPOUNDS AND METHODS FOR CHANGING CALCIUM METABOLISM WITHIN THE CELLS OF A MAMMAL

The invention described herein was made in the course of work under a grant #HL 21670 made by the U.S. Department of Health and Human Services.

BACKGROUND OF THE INVENTION

The invention relates to compounds and methods for changing calcium metabolism within the cells of a mammal.

Calcium ions appear to play an important role in innumerable physiological body functions in mammals. Thus, calcium ions are involved in blood clotting and coagulation, cellular adhesion, integrity and membrane stability, bone and teeth formation, enzyme activity, control of certain aspects of cyclic nucleotide metabolism, mediation of certain activities of prostaglandins, cell division, muscle contraction, glandular and other cellular secretory functions, neuronal transmission and numerous other physiological functions. Calcium also effects the pharmacological and toxicological actions of many drugs and chemicals. Accordingly, it is not surprising that the pharmaceutical efficacy of many drugs is dependent at least in part upon their calcium antagonist activity, although in most cases it has only recently been recognized that it is the calcium antagonist activity of the drug which is responsible for its pharmaceutical activity. Such drugs include local anesthetics, anticonvulsants, antiarrhythmics, coronary dilators, antihypertensives and skeletal muscle relaxants as well as other types of drugs.

The calcium required for the aforementioned physiological functions may be derived from either extracellular sources (basement membrane, ground substance or extracellular fluids) or intracellular calcium storage pools (mitochondria, endoplasmic reticulum, nucleus, the inner aspect of the plasma membrane and possibly secretory vesicles). Calcium antagonist drugs may operate either by affecting the rate at which calcium is transported into the cell from extracellular sources or by affecting the metabolism of intracellular calcium (by inhibiting the action or mobilization of intracellular calcium, by enhancing the sequestration of calcium ion by intracellular organelles or by altering its rate of efflux from the cell). The former group of calcium antagonist drugs are known as calcium entry blockers and include local anesthetics, manganese, lanthanum, phenytoin, barbiturates, Org 6001 (3α-amino-2β-hydroxy-5α-androstan-17-one), methadone, 1-acetylmethadol, 1-pentazocine, dantrolene, nitroglycerine and other nitrites and organic nitrates, indomethacin, adrenergic $\beta_2$-receptor agonists, morphine, alcohol, aminoglycoside antibiotics such as streptomycin and neomycin, SKF-525A, R33711, flunarizine, cinnarizine, hydralazine, lidoflazine, bepridil, cinepazet maleate, hexoestrol and the prenylamine group of compounds including prenylamine itself, verapamil, methoxyverapamil (D600), fendiline, nifedipine, ditiazem, perhexiline and FR 7534. The physiological action of most of the calcium entry blockers is complicated by the fact that they also block the entry of sodium into the cell and this can make their activity difficult to predict.

The other main group of calcium antagonists which act on intracellular calcium are known as intracellular calcium antagonists and include magnesium, sodium nitroprusside, diazoxide, dantrolene, ryanodine, and the ω-(N,N-diethylamino) alkyl-3,4,5-trimethoxybenzoates.

We have previously synthesized 2-alkyl-5,6-methylenedioxyindene-1-dimethylammonium salts wherein the 2-substituent is an n-propyl or n-butyl group. Although these compounds were obtained as intermediates in the synthesis of potential prostaglandin antagonistic end products, screening of the compounds for potential prostaglandin receptor antagonistic activity of isolated rat uteri showed that these compounds were not selective prostaglandin blockers but indicated that they appear to be calcium antagonists. Our further work on these compounds has indicated that they are indeed intracellular calcium antagonists. In particular, we have shown that these two compounds inhibit rodent nonvascular smooth muscle contraction, bovine coronary vessel constriction and bovine adrenomedullary catecholamine secretion. The compounds have also been shown to increase coronary flow and decrease cardiac inotropic activity in isolated rabbit heart preparations. Moreover, the compounds have been shown to have significant antiarrhythmic activity against ouabain-arrhythmias in dogs, and our further work shows them to be effective against calcium-induced arrhythmias in dogs and rats, aconitine-induced and methacoline-induced arrhythmias in rats and chloroform-/anoxia-induced arrhythmias in mice. This further work of ours shows that in the calcium-induced arrhythmia model in rats, both the propyl and butyl compounds were more potent and safer than verapamil, which is one of the standard drugs used in this field. In the chloroform/anoxia-induced arrhythmia model in mice, the butyl compound was more potent than quinidine and the propyl compound was as potent as quinidine. Earlier published work of ours has shown both the propyl and the butyl compounds show a remarkable lack of toxicity when tested acutely and subchronically.

The synthesis and physiological activity of the aforementioned dimethylaminoindenes are described in the following papers:

I. D. T. Witiak, D. R. Williams, S. V. Kakodkar, G. Hite and M. S. Chen, *J. Org. Chem.*, 39, 1242 (1974).

II. R. G. Rahwan, M. M. Faust and D. T. Witiak, *J. Pharmacol. Exp. Ther.*, 201, 126 (1977).

III. M. F. Piascik, R. G. Rahwan and D. T. Witiak, *J. Pharmacol. Exp. Ther.*, 205, 155 (1978).

IV. D. T. Witiak, S. V. Kakodkar, T. P. Johnson, J. R. Baldwin and R. G. Rahwan, *J. Med. Chem.*, 22, 77 (1979).

V. C. E. Akesson, R. G. Rahwan, D. T. Witiak, R. J. Brumbaugh, *Res. Commun. Chem. Pathol. Pharmacol.* 27, 265, (1980).

VI. R. G. Rahwan, M. F. Piascik, D. T. Witiak, *Canad. J. Physiol. Pharmacol*, 57, 433, (1979).

VII. M. F. Piascik, R. G. Rahwan and D. T. Witiak, *J. Pharmacol. Exp. Ther.*, 210, 141 (1979).

VIII. M. F. Piascik, M. T. Piascik, D. T. Witiak and R. G. Rahwan, i Canad. J. Physiol. Pharmacol., 57, 1350 (1979); and IX. R. G. Rahwan, C. E. Akesson and D. T. Witiak, *Res. Commun. Chem. Pathol. Pharmacol.* 26, 85 (1979).

We have now synthesized derivatives of the aforementioned propyl and butyl aminoindenes and related compounds. Certain of these new derivatives exert a more powerful pharmacological activity than the aforementioned aminoindenes from which they are derived.

SUMMARY OF THE INVENTION

The calcium antagonist compounds of the invention are the compounds of Formulae II, IIA, IIIB, IVA, and IVB of the accompanying Reaction Scheme together with the salts of the tertiary amines of Formulae IIIA and IIIB. In each of these formulae $R_2$ is an alkyl group of 1 to about 8 carbon atoms, each $R_3$ independently is an alkyl group of 1 to 3 carbon atoms $X^-$ is an anion, and each $R_1$ independently is an alkyl group of 1 to 3 carbon atoms or the two $R_1$ groups together form an alkylene group of 1 to 3 carbon atoms.

Each $R_1$ is preferably a methyl group or the two $R_1$ groups together form a methylene group, the latter compounds being especially preferred. In all the compounds, $R_2$ is preferably an alkyl group of 2 to about 5 carbon atoms, most preferably 3 or 4 carbon atoms and is desirably n-propyl or n-butyl, each $R_3$ is preferably a methyl group and $X^-$ is preferably a halide ion, most desirably a chloride or iodide ion.

It will be appreciated that the compounds of Formulae IIIA and IVA are cis-isomers, while the compounds of Formulae IIIB and IVB are the corresponding trans-isomers. The invention extends to both the cis and trans-isomers either in the form of the pure isomers or as a mixture thereof.

Specific preferred compounds of Formula II are 2-propyl; and 2-butyl-5,6-methylenedioxyindene-1-trimethylammonium iodides. Specific preferred compounds of Formulae IIIA and IIIB are 2-propyl; and 2-butyl-5,6-methylenedioxyindane-1-dimethylamine and their hydroiodides. Specific preferred compounds of Formulae IVA and IVB are the cis- and trans-isomers of 2-propyl; and 2-butyl-5,6-methylenedioxyindene-1-trimethylammonium iodides.

The invention also provides a method for changing calcium metabolism within the cells of a mammal which comprises administering to the mammal a pharmaceutically-effective amount of a compound of Formula II, IIIA, IIIB, IVA or IVB or a pharmaceutically-acceptable salt of a compound of Formula IIIA or IIIB. The mammal may be one suffering from arrhythmia and the pharmaceutically-acceptable amount of the compound administered preferably comprises from about 0.25 to about 10 mg/kg body weight of the mammal.

It will be noted that the compounds of Formulae II, IVA and IVB above are quaternary amines. The pharmaceutical activity of such quaternary compounds demonstrated by our previously-published results set out in papers II and III above suggests that the compounds of Formula I have an intracellular site of action. Since in general ionized compounds do not pass cell membranes, this suggests that the compounds of Formula I reach their intracellular site of action in the non-ionic, free base form. Since no comparable free base form exists for the quarternary compounds of Formulae II, IVA and IVB, the quarternary compounds would be expected to be inactive whereas, as shown below, the quaternary compounds are more active than the compounds of Formula I.

Obviously, when one of the instant salts is to be used pharmaceutically, the salt must be one having a pharmaceutically-acceptable anion, for example a halide, nitrate or a sulphate. However, the invention extends to the salts having a non-pharmaceutically-acceptable (i.e. toxic) anion both because such salts are useful in preparing the salts having pharmaceutically-acceptable anions and because the non-pharmaceutically-acceptable salts may represent a more convenient storage form of the compounds than the pharmaceutically-acceptable salts.

BRIEF DESCRIPTION OF THE DRAWING

The accompanying Reaction Scheme shows the reactions employed to produce the compounds of the invention.

DETAILED DESCRIPTION OF THE INVENTION

All the compounds of the invention may be prepared from a 2-alkyl-5,6-dialkoxyindene-dialkylammonium salt of Formula I (hereinafter, references to 5,6-dialkoxy compounds should be construed to include both the true 5,6-dialkoxy compounds, wherein the two R groups are separate alkyl groups, and the 5,6-alkylenedioxy compounds, in which the two R groups together form an alkylene group). The preparation of some of the compounds of Formula I is described in paper I mentioned above; the mode of preparation of the other compounds of Formula I may be effected by modification of the process described in that paper which will be obvious to those skilled in the art.

The quaternization of the compounds of Formula I to produce the corresponding compounds of Formula II may be effected by any of the known methods for the quaternization of secondary amines. Conveniently, the quaternization is effected by reaction of the compound of Formula I with the appropriate alkyl halide $R_3X$ to produce the halide salt of Formula II. Conveniently, the reaction is carried out in solution in an alcohol such as absolute ethanol with excess alkyl halide present. If it is desired to prepare a salt of Formula II in which the anion $X^-$ is not a halide, the nonhalide salt may be prepared from the halide salt by simple metathesis.

The hydrogenation of the compounds of Formula I to produce the 2-alkyl-5,6-dialkoxyindene-1-dialkylamines of Formula IIIA or IIIB and their salts may be effected by any conventional hydrogenation technique but is conveniently effected by passing hydrogen gas through a solution of a compound of Formula I or the corresponding free amine containing a transition metal catalyst such as Raney nickel or finely divided platinum or palladium. The hydrogenation reaction is conveniently carried out in solution in alcohol. It has been found that the hydrogenation reaction produces a major proportion of the cis-isomers of Formula IIIA and only a minor proportion of the trans-isomer of Formula IIIB. The two isomers may be separated by thin layer or column chromatography. If the hydrogenation is effected on a salt of Formula I and it is desired to produce a free amine of Formula IIIA or IIIB, the free amine may of course be liberated from the salt produced simply by the addition of alkali.

For pharmaceutical use, the compounds of Formulae IIIA and IIIB may be in the form of the pure cis or trans-isomer or any mixture of these two isomers.

To prepare a salt of a compound of Formula IIIA or IIIB having an anion different from that of the starting material of Formula I, the anion may be changed by simple metathesis either before or after the hydrogenation reaction.

The quaternization of the compounds of Formuae IIIA and IIIB to produce the 2-alkyl-5,6-dialkoxyindene-1-trialkylammonium salts of Formula IVA or IVB respectively is achieved by the same methods as the quaternization of the compounds of Formula I to produce the compounds of Formula II. Again, if a change of anion is desired, this change may be effected by simple metathesis.

It will be appreciated that the compounds of Formulae IVA and IVB may theoretically by produced by hydrogenation of a compound of Formula II. However, solubility problems in hydrogenating the quaternary compounds of Formula II make it much more convenient to produce the compounds of Formulae IVA and IVB via the compounds of Formulae IIIA and IIIB and their salts.

The compounds of the invention are, as already stated, useful for altering calcium metabolism in mammals. As shown by the animal test results below, compounds of Formula II are substantially more potent in protecting mammals against arrhythmias, in particular aconitine, chloroform, calcium, and methacholine-induced arrhythmias, than the compounds of Formula I and are less toxic to mammals than the compounds of Formula I.

It should be noted that to secure the proper calcium antagonist activity, the group $R_2$ in each of the active compounds should preferably be an alkyl group of 2 to about 5 carbon atoms, alkyl groups containing 3 or 4 carbon atoms being most efficacious. Compounds having $R_2$ groups outside this range tend to be less pharmaceutically useful.

The following Examples and animal test results are now given, though by way of illustration only, to describe the preparation and pharmaceutical utility of specific preferred compounds of the invention.

EXAMPLE 1

Preparation of 2-butyl-5,6-methylenedioxyindene-1-trimethylammonium iodide

This Example illustrates the preparation of the compound of Formula II in which the two $R_1$ groups together form a methylene group, $R_2$ is n-butyl, each $R_3$ is methyl and $X^-$ is an iodide ion.

50 g. was 3,4-methylenedioxybenzaldehyde (0.33 moles) in 500 ml of ether was reacted with 56.2 g. of n-butyllithium in approximately 360 ml of hexane to produce 68 g (98% of theoretical) of crude 1-(3,4-methylenedioxyphenyl)-pentan-1-ol, which was used in the following step without further purification.

The whole 68 grams of this crude product was fused with 3.5 g. of potassium bisulfate to yield 52 g. (84% of theoretical) of semi-pure 1-(3,4-methylenedioxyphenyl)-pent-1-ene exclusively in the form of the trans-isomer. The semi-pure product, which had already been washed to remove the salt, was used in the following step without further purification.

The whole 52 grams of the semi-pure product was treated with dimethylformamide and phosphorus oxychloride and then, after separation of the intermediate product from the dimethylformamide and the phosphorus oxychloride, with dry hydrogen chloride to yield 2-propyl-5,6-methylenedioxyindene-1-dimethyl ammonium chloride. The yield of pure compound was 25 g., 33% of theoretical; however, using pure olefin yields of approximately 70% are obtained in this reaction.

Except that a different procedure was used in the dehydration step, the above preparation is substantially in accordance with paper I above. 2-Butyl-5,6-methylenedioxyindene-1-dimethylammonium chloride was prepared in precisely the same manner using n-pentyllithium in place of the n-butyllithium in the first step of the process, and 1 g. (0.0034 moles) of this hydrochloride was converted to the free base by dissolving the salt in a mixture of 10 ml. of absolute ethanol and 15 ml. of distilled water. The solution was made alkaline with 10% aqueous sodium hydroxide solution and extracted with three 25 ml. aliquots of ether. The combined ether extracts were dried over anhydrous sodium sulfate and the ether was removed under reduced pressure. The oily residue was confirmed as the free amine by its NMR spectrum. The residue was dissolved in 25 ml. of absolute ethanol. 1.5 ml. of methyl iodide was added and the solution was stirred for 24 hours at room temperature. A light yellow solid was separated from the solution by vacuum filtration, washed with absolute ethanol and dried in air to give the crude quaternary iodide. The crude product was recrystallized from a 1:20 ethanol:ether mixture to yield pale yellow needles melting at 150°–151° C. with decomposition and having the expected NMR spectrum showing nine methyl protons. Elemental analysis yielded the following results:

$C_{17}H_{24}NO_2I$—Calculated: C 50.88; H 6.03; N 3.49. Found: C 50.93; H 6.06; N 3.49.

2-propyl-5,6-methylenedioxyindene-1-trimethylammonium iodide may be prepared in the same manner from 2-propyl-5,6-methylenedioxyindene-1-dimethylammonium chloride.

EXAMPLE 2

Preparation of 2-propyl-5,6-methylenedioxyindane-1-dimethylammonium chloride

This Example shows the preparation of a mixture of the compounds of Formulae IIIA and IIIB in which the two $R_1$ groups together form a methylene group, $R_2$ is n-propyl, each $R_3$ is methyl and $X^-$ is a chloride ion, and the separation of the cis and trans-isomers.

1 g. (0.0035 mole) of 2-propyl-5,6-methylenedioxyindene-1-dimethylammonium chloride prepared in Example 1 above was dissolved in 100 ml. of absolute ethanol. A catalytic amount of platinum dioxide was added and this mixture was hydrogenated over a 15 hour period at room temperature and under a hydrogen pressure of 50 lb. in.$^{-2}$. The platinum dioxide catalyst was removed by filtration and the ethanol was removed under reduced pressure to give 1 g. of a crude isomeric mixture. Recrystallization from a mixture of dry ether and absolute ethanol, with addition of charcoal for decolorization, gave 510 mg. (32% of theoretical) of a pure cis product having a melting point of 184°–185° C.

The absence of olefinic protons in the NMR spectrum provided additional evidence that the product was 2-propyl-1-dimethylamino-5,6-methylenedioxyindane hydrochloride. Separation of the cis and trans-isomers from a sample of the crude product was effected by column chromatography on silica gel using ethyl acetate as eluant. The pure cis-isomer isomer exhibited a coupling constant J=2.5 Hz between the protons on $C_1$, and $C_2$, while the trans-isomer had J=7.8 Hz for the same protons (the coupling constants were in both cases measured on the free bases in solution in deuterochloroform). The trans isomer had a melting point of 187°–188° C. and both isomers showed the expected elemental analyses. The reaction proceeded virtually quantitatively, the product being approximately 93% cis and 7% trans.

EXAMPLE 3

Preparation of 2-propyl-5,6-methylenedioxyindane-1-dimethylammonium chloride This example shows the preparation of a mixture of the compounds of Formulae IIIA and IIIB in which the two $R_1$ groups together form a methylene group, $R_2$ is n-propyl, each $R_3$ is methyl and $X^-$ is a chloride ion, and the separation of the pure cis-isomer.

The compounds were prepared using the same technique as in Example 2 above. 1 . (0.0035 mole) of 2-butyl-5,6-methylenedioxyindane-1-dimethylammonium chloride prepared in Example 1 above was dissolved in 100 ml of absolute ethanol. A catalytic amount of platinum dioxide was added and the mixture was hydrongenated over a 15 hour period at room temperature and under a hydrogen pressure of 50 lb. in.$^{-2}$. The platinum dioxide catalyst was removed by filtration and the ethanol distilled off under reduced pressure to give 0.95 g. of a viscous oil which solidified on standing. Analysis of this crude product by thin layer chromatography using as solvent a 1:1 mixture of acetonitrile and isopropanol slightly acidified with glacial acetic acid showed the crude product to contain two components (the cis and trans-isomers of the indane product) and not to be contaminated with indene starting material. Recrystallization of the crude product from a mixture of dry ether and absolute ethanol, with addition of charcoal for decolorization gave 320 mg. (32% of theoretical) of a pure product having a melting point of 184°–185° C. and shown by its NMR coupling constants to be the pure cis-indane.

EXAMPLE 4

Preparation of cis-2-propyl-5,6-methylenedioxyindane-1-trimethylammonium iodide This example shows the preparation of a compound of Formula IVA in which the two R groups together form a methylene group, $R_2$ is n-propyl, each $R_3$ is methyl and $X^-$ is a iodide ion.

0.65 g. (0.0023 moles) of cis 2-propyl-5,6-methylenedioxyindane-1-trimethylammonium chloride prepared as Example 2 above was converted to the free base with alkali and dissolved in 25 ml. of absolute ethanol. 1.5 ml. of methyl iodide was added and the solution was stirred for 24 hours at room temperature. The ethanol and excess methyl iodide were then removed by distillation under reduced pressure leaving a residue of the crude quaternary iodide. The crude product was recrystallized from a 1:20 ethanol:ether mixture to yield pale yellow needles having the expected NMR spectrum. Analysis calculated for $C_{16}H_{24}NO_2I\frac{1}{2}H_2O$: C, 48.25; H, 6.47; N, 3.52 Found C, 48.32; H, 6.51; N, 3.46.

ANIMAL TEST RESULTS

Aconitine-induced arrhythmias

2-Butyl-5,6-methylenedioxyindene-1-trimethylammonium iodide (the compound prepared in Example 1 above and hereinafter abbreviated as Q-bu-MDI) was compared with quinidine, 2-butyl-5-6-methylenedioxyindene-1-dimethylammonium hydrochloride (the starting material used in Example 1 and hereinafter abbreviated as bu-MDI), and the corresponding 2-propyl compound (hereinafter abbreviated as pr-MDI) for its effect in protecting against aconitine induced arrhythmias in rats.

The antiarrhythmic activity of the compound was evaluated by the method described in Haas von H, Busch E: Antiarrhythmische Wirkungen von Verapamil and seinen Derivaten im Vergleich zu Propanolol, Pronetalol, Chinidin, Procainamid und Ajamilin, *Arzneim Forsch* 4: 401–407, 1968. Male Sprague-Dawley rats obtained from the Laboratory Supply Company, Indianapolis, Indiana, weighing 180–250 g. were anesthetized with sodium pentobarbital. The left jugular vein was cannulated for drug administration and the electrocardiograph lead II was monitored by a Physiograph Mark III preamplifier and recorded on a Physiograph DMP-4-B recorder obtained from E & M Instrument Company, Houston, Texas. The compound under test was injected into the jugular vein five minutes before the start of an intravenous infusion of 10 µg/kg/min of aconitine delivered at a constant rate of 0.136 ml/min by a Model 901 withdrawal/infusion pump obtained from Harvard Apparatus Company, Mills, Mass. The electrocardiograph was continuously monitored until the onset of ventricular arrhythmias, which usually consisted of a series of downward deflections with enlarged QRS complexes. The first continuous burst of such downward deflections lasting five seconds or more was chosen as the end point. The compounds under test were administered in a 5% dextrose solution, while the aconitine was dissolved in distilled water to which a few drops of 2 N hydrochloric acid had been added.

The lowest dose of quinidine which provided significant protection against aconitine-induced arrhythmias was 8 mg/kg, while that for bu-MDI was 16 mg/kg, that for pr-MDI was 24 mg/kg and that for Q-bu-MDI was 0.25 mg/kg.

Thus, Q-bu-MDI was approximately 32 times as effective in this test as the conventional quinidine. In addition, at the effective doses of 0.25 and 1 mg/kg, Q-bu-MDI produced insignificant tachycardia ($+2.6\pm1.0\%$ and $+2.3\pm3.0\%$ respectively at these two concentrations) during the pretreatment. Q-bu-MDI only produced problems at the higher dose of 4 mg/kg where there was significant bradycardia, P wave inversion and atrioventricular dissociation, along with concomitant loss of anti-arrhythmic activity. The other three compounds tested showed significant effects on the heart rate at the lowest concentrations at which they were effective in overcoming the aconitine-induced arrhythmia. At the minimum protective dose of 8 mg/kg, quinidine decreased the heart rate ($-7.8\pm0.9\%$) and severely deepened the S wave. At its minimum effective dose of 16 mg/kg, bu-MDI significantly reduced the heart rate ($-18.7\pm2.2\%$) and a slight increase in QRS amplitude was evident. A further increase of 50% in bu-MDI concentration to 24 mg/kg resulted in clear signs of toxicity including severe bradycardia ($-28.9\pm3.6\%$), marked increase in QRS amplitude and severe deepending of the S wave, with concomitant loss of antiarrhythmic activity.

At its minimum effective dose of 24 mg/kg, pr-MDI produced bradycardia ($-28.9\pm4.4\%$), a modest increase in QRS amplitude and slight deepening of the S wave.

Thus, of the four compounds tested, not only was Q-bu-MDI the most effective, but it showed the fewest side effects at its minimum effective concentration.

Methacholine-induced arrhythmias

The same four compounds were tested for their ability to protect rats from methacholine-induced arrhythmias, the compounds again being administered by intravenous injection.

The experimental method employed was similar to that described above for aconitine-induced arrhythmias. The compound under test was injected into the jugular vein five minutes before starting an intravenous infusion of 80 μg/kg/min of acetyl-β-methylcholine chloride (methacholine) delivered at a constant rate of 0.136 ml/min. The electrocardiogram was monitored continuously until the onset of a consistant, characteristic atrioventricular dissociation which was considered the end point. The compounds under test were delivered in a 5% dextrose solution, while the methacholine was dissolved in distilled water acidified to pH 4.

The minimum effective dosage of quinidine was 4 mg/kg, for bu-MDI 2 mg/kg, for pr-MDI 4 mg/kg, and for Q-bu-MDI 1 mg/kg.

Although quinidine offered protection against methacholine-induced arrhythmias at 4 mg/kg, deleterious effects on the electrocardiogram and heartbeat similar to those noted above in the tests on aconitine-induced arrhythmias were noted at this dosage. At its minimum effective dose of 2 mg/kg, bu-MDI exhibited virtually no intrinsic effects on heart rate or the normal electrocardiogram during the pre-treatment. Similarly, at the minimum effective dosage of 4 mg/kg pr-MDI had no intrinsic effect on the normal electrocardiogram and only produced a slight bradycardia (as noted in the aconitine-induced arrhythmia tests) was observed. The minimum protective dosage of Q-bu-MDI (1 mg/kg) also produced no intrinsic effects on the normal electrocardiogram and only a slight tachycardia (+9.3±1.8%).

Thus, not only was Q-bu-MDI effective at lower dosage than the other compounds tested, but Q-bu-MDI can be used with minimal side effects at its minimum effective dosage, whereas the conventional qinidine exhibits significant deleterious side effects at its minimum effective condensation.

Calcium-Induced Arrhythmias

The same four compounds were tested for their ability to protect rats from calcium-induced arrhythmias, the compounds again being administered by intravenous injection. The experimental method used was that described in Lynch J. J., Rahwan R. G., Witiak D. T.: Effects of 2-substituted-3-dimethylamino-5,6-methylenedioxyindenes on calcium-induced arrhythmias, *J. Cardiovasc. Pharmacol.* 3: 49–60 (1981). The compound under test, dissolved in 5% dextrose solution, was administered into the jugular vein of anesthetized rats over a 40 second period. Ten minutes after this treatment, an acute dose of 1 ml/kg of a 10% $CaCl_2.2H_2O$ solution was injected into the jugular vein over a period of 10 seconds. The arrhythmias resulting from the calcium administration were graded according to the following criteria: (a) initial change in heart rate following calcium administration; (b) incidences of sinoatrial block, atrioventricular block, ectopic beats, and ventricular flutter and fibrillation; (c) time required for reversion to control ECG; and (d) incidence of mortality.

In controls to which no protective agent was administered, the acute dose of calcium chloride elicited arrhythmias. Within 30 seconds of the calcium administration profound bradycardia occurred. Complex arrhythmias, comprising predominantly sinoatrial block, second and third degree atrioventricular block, nodal and ventricular ectopic beats and ventricular flutter and fibrillation, occurred in 95% of the control animals during and after the initial bradycardia, causing mortality of 30% of the controls. The mean time for reversion to control electrocardiogram in surviving animals was 332±57 seconds.

The Q-bu-MDI at a concentration of 0.5 mg/kg afforded partial protection against the calcium-induced bradycardia, almost complete protection against arrhythmia and complete protection against calcium-induced mortality, and also significantly reduced the time for reversion to a normal electrocardiogram. At this dosage, Q-bu-MDI exhibited no substantial deleterious side effects.

Pr-MDI and bu-MDI were also effective in protecting the rats against calcium-induced arrhythmias without deleterious side effects, but only at a concentration of 3.75 mg/kg. Quinidine was effective only at a concentration of 8 mg/kg, at which concentration it afforded partial protection against calcium-induced bradycardia, almost complete protection against arrhythmia and complete protection against calcium-induced mortality; at this concentration, quinidine also significantly reduced the time to reversion to the control electrocardiogram. However, at this concentration the quinidine produced significant deleterious side effects, as described above in relation to aconidine-induced arrhythmias.

Thus, in this test Q-bu-MDI was approximately 16 times as effective as the conventional drug quinidine without producing quinidine's deleterious side effects.

Chloroform Anoxia Assay

The same four compounds were tested for their ability to protect mice from chloroform anoxia by the classical chloroform inhalation procedure described in Lawson J. W.: Antiarrhythmic activity of some isoquinoline derivatives determined by a rapid screening procedure in the mouse, *J. Pharmacol. Exp. Ther.* 160: 22–31, (1968). In this method, chloroform inhalation leading to respiratory arrest produces ventricular fibrillation. Female Swiss albino mice procured from Laboratory Supply Company, Indianapolis, Ind., weighing 16–22 g, were pretreated intraperitoneally with the compound under test dissolved in a 5% dextrose solution 10 minutes before exposure to chloroform in a closed container containing chloroform-saturated cotton. The mice were removed from the chloroform atmosphere immediately after respiratory arrest and the electrocardiograph lead II monitored. The ED 50 and 95% confidence limits calculated for the anti-arrhythmic agents by the standard method of Litchfield and Wilcoxon.

The ED 50's were:
Q-bu-MDI 10.5 mg/kg
bu-MDI 44 mg/kg
quinidine 67 mg/kg
pr-MDI 68 mg/kg.

Slope functions and tests for parallelism of anti-arrhythmic dose-response curves indicated that the regression lines for the three indenes were parallel to that of quinidine ($p < 0.05$) and that the ED 50 of Q-bu-MDI was significantly smaller than that of quinidine $p << 0.05$).

Toxicity Tests

The LD intraperitoneal 50's of the four compounds tested above and verapamil were tested in mice by the method set out in Paper IX above or similar standard procedures, the experimental values obtained being:
Q-bu-MID 65 mg/kg
bu-MDI 185 mg/kg
pr-MDI 185 mg/kg
quinidine 225 mg/kg
verapamil 68 mg/kg.

Comparing the LD 50's of the first four compounds mentioned above with the corresponding ED 50's obtained in the chloroform anoxia tests described above, the therapeutic indices of the compounds are shown in the following table:

|  | $n^a$ | $ED_{50}^b$ (mg/kg, i.p.) | $LD_{50}^b$ (mg/kg, i.p.) | Therapeutic Index ($LD_{50}/ED_{50}$) | Antiarrhythmic Potency |
|---|---|---|---|---|---|
| Quinidine | 40 | 67.0 (53.3–84.2) | 225 (210–241) | 3.1 | 1.00 |
| Pr-MDI | 40 | 68.0 (52.3–83.4) | 185 (171.3–199.8) | 2.7 | 0.99 |
| Bu-MDI | 40 | 44.0 (34.1–56.7) | 185 (171.3–199.8) | 4.2 | 1.52 |
| Q-bu-MDI | 40 | 10.5 (4.0–27.9) | 65 (56.8–74.4) | 6.2 | 6.38 |

$^a$Number of pretreated mice exposed to chloroform.
$^b$Mean values and 95% confidence limits.

Thus, Q-bu-MDI is greatly superior to the known compounds quinidine, pr-MDI an bu-MDI as an antiarrhythmic agent.

Effects on Isolated Guinea Pig Atria

The effects of pr-MDI, bu-MDI and Q-bu-MDI on the methanical and electrical behavior of isolated guinea pig atria were investigated by the method of H. Nawrath, *J. Pharmacol. Exp. Ther.*, 16, 176–182 (1980). The compounds were investigated over the concentration range of $10^{-8}$ to $3 \times 10^{-4}$ M. Q-bu-MDI caused a very modest, dose-dependent decrease in the contractile force of the electrically-stimulated left atrium; the decrease varied from 10% at a concentration of $3 \times 10^{-6}$ M to a maximum decrease of approximately 20% at $10^{-4}$ M. At $3 \times 10^{-4}$ M, there was a partial reversal of this negative inotropic effect. The modest negative inotropy displayed by Q-bu-MDI in the electrically-stimulated left atrium was also observed in the non-stimulated right atrium. The administration of $3 \times 10^{-4}$ M Q-bu-MDI produced no persistent effects, the frequency-force relation of the stimulated left atrium a short while following administration of the Q-bu-MDI was the same as that prior to treatment with this compound, and the threshold voltage required to drive the left atrium was also unchanged following administration of Q-bu-MDI at $3 \times 10^{-4}$ M. Q-bu-MDI also caused a very slight decrease in the spontaneous atrial rate, this decrease being less than 10% over the concentration range $10^{-8}$ to $3 \times 10^{-5}$ M and increasing to approximately 20% at $3 \times 10^{-4}$ M. Bu-MDI produced a much greater, dose-dependent decrease in the contractile force of the stimulated atrium varying from about 20% at $3 \times 10^{-6}$ M to approximately 70% at $3 \times 10^{-4}$ M. This much more marked inotropic property of bu-MDI was also reflected in the behavior of the non-stimulated right atrium. Treatment of the electrically-stimulated atrium with $3 \times 10^{-4}$ M bu-MDI produced significant depression of the frequency-force profiles depressing the tension developed at all stimulation frequencies and invariably rendering the tissue less able to follow higher frequencies stimulation. Furthermore, treatment of the left atrium with $3 \times 10^{-4}$ M bu-MDI significantly decreased the threshold voltage required to drive the atria. Bu-MDI produced only a very slight decrease in the spontaneous artrial rate, substantially identical to that produced by Q-bu-MDI.

Pr-MDI, in preliminary tests, gave results indicating that it had a negative inotropic activity at least as great as, and possibly greater than, bu-MDI. Pr-MDI also depressed the developed tension in the left atrium at various stimulation frequencies and increased the threshold voltage for driving the left atrium. The effect of pr-MDI on the spontaneous atrial rate appears to be substantially the same as that of the other two compounds tested.

Thus, Q-bu-MDI has a markedly small effect than bu-MDI or pr-MDI upon electrical and mechanical activity in guinea pig atria. Q-bu-MDI produces very modest decreases in spontaneous atrial rate and stimulated atrial force of contraction and has no significant effect upon the threshold voltage for stimulation or the frequency-force relation of the atrium. In as much as decreases in the contractive force generated by the atrium are deleterious to a mammal being treated with the drug, because such decreases in contractive force tend to cause congestive heart failure and coronary steal phenomena, the above tests indicate that Q-bu-MDI would have less side effects upon the heart than pr-MDI or bu-MDI.

Vasodilator Activity

Pr-MDI, bu-MDI, Q-bu-MDI and the compounds of Formulae IIIA and IIIB having the two $R_1$ groups together forming a methylene group, each $R_3$ a methyl group and $R_2$ an n-propyl group or n-butyl group (the last two compounds are hereinafter abbreviated as sat-pr-MDI and sat-bu-MDI respectively, reference being made where necessary to the cis isomer of Formula III A or the trans isomer of Formula III B) were tested for vasodilator activity by the method of R. F. Furchgott and S. Bhadrakom, *J. P. Pharmacol. Ex. Ther.*, 108, 129–143 (1953). Sprague-Dawley rats weighing 250–350 g., obtained from the same source as above, were sacrificed and spirally cuts strips of the thoracic aorta were mounted in isolated tissue baths held at a temperature of 37° C. After equilibration for one hour in a physiological buffer solution, the strips were contracted for 30 minutes with either an isotonic high-potassium buffer having a potassium concentration of 40 mM or with norepinephrine at a concentration of $10^{-7}$ M. The spasmolytic activity of each compound was then tested by adding it in increasing concentrations to the solution bathing the tissue.

Each of the compounds tested relaxed the aortic tissue in a concentration-dependent manner. On potassium-contracted aorta tissue, pr-MDI and bu-MDI had closely similar potency ($IC_{50}=2.2 \times 10^{-5}$ M and $2.1 \times 10^{-5}$ M respectively), but Q-bu-MDI was substantially less active ($IC_{50}=1.6 \times 10^{-4}$ M). However, with norepinephrine-contracted aortic tissue (which is a more physiologically realistic model than potassium-contracted tissue, especially since persons suffering from heart disease tend to have elevated norepinephrine levels), pr-MDI, bu-MDI and Q-bu-MDI demonstrated similar potency in relaxing the aortic tissues ($IC_{50}=7.9\times10^{-5}$ M, $8.7\times10^{-5}$ M and $1.1\times10^{-4}$ M respectively). Cis sat-pr-MDI had a potency on both potassium and norepinephrine-contracted aortic tissue substantially equal to that of pr-MDI ($IC_{50}=3.1\times10^{-5}$ M and $6.2\times10^{-5}$ M for potassium and norepinephrine-contracted tissue respectively). However, trans sat-pr-MDI was markedly less active than its unsaturated analogue ($IC_{50}=1.0\times10^{-4}$ M and $3.8\times10^{-4}$ M for potassium and norepinephrine-contracted tissue respectively). Cis sat-bu-MDI had a potency ($IC_{50}=1.7\times10^{-4}$ M) similar to that of bu-MDI on potassium-contracted aortic tissue but was significantly ($IC_{50}=3.4\times10^{-5}$ M) more potent than its unsaturated analogue in reversing norepinephrine-contracted aortic tissue.

The above results indicate that the cis-compounds of Formula IIIA are at least as potent in their effect on aortic tissue as their unsaturated analogues of Formula I. Thus, the compounds of Formula IIIA are expected to possess vasodilating and antihypertensive activity similar to that already demonstrated for the compounds of Formula I.

On the basis of the similarity of the action of the instant compounds to the known compounds bu-MDI and pr-MDI, it is believed that in addition to being useful for the treatment of arrhythmia, the instant compounds will also be useful for the treatment of hypertension, for coronary dilation (for example as anti-angina pectoris agents).

We claim:

1. A 2-alkyl-5,6-dialkoxyindene-1-trialkylammonium salt of Formula II

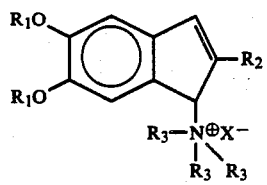

wherein the two $R_1$'s together form an alkylene group of 1 to 3 carbon atoms, $R_2$ is an alkyl group of 1 to about 8 carbon atoms, a cycloalkyl group of 3 to about 7 carbon atoms or a phenyl group, each $R_3$ independently is an alkyl group of 1 to 3 carbon atoms and $X^-$ is an anion.

2. A salt according to claim 1 wherein the two $R_1$ groups together form a methylene group.

3. A salt according to claim 1 wherein $R_2$ is an alkyl group of 2 to about 5 carbon atoms.

4. A salt according to claim 3 wherein $R_2$ is an alkyl group of 3 or 4 carbon atoms.

5. A salt according to claim 4 wherein $R_2$ is n-propyl or n-butyl.

6. A salt according to claim 1 wherein each $R_3$ is a methyl group.

7. A salt according to claim 1 wherein $X^-$ is a halide ion.

8. A salt according to claim 7 wherein $X^-$ is a chloride or iodide ion.

9. The salt according to claim 1 wherein the two $R_1$ groups together form a methylene group, $R_2$ is n-propyl, each $R_3$ is methyl and $X^-$ is an iodide ion, namely 2-propyl-5,6-methylenedioxyindene-1-trimethylammonium iodide.

10. The salt according to claim 1 wherein the two $R_1$ groups together form a methylene group, $R_2$ is n-butyl, each $R_3$ is methyl and $X^-$ is an iodide ion, namely 2-butyl-5,6-methylenedioxyindene-1-trimethylammonium iodide.

11. A cis 2-alkyl-5,6-dialkoxy-1-dimethylaminoindane of Formula IIIA

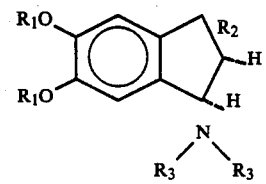

wherein the two $R_1$ groups together form an alkylene group of 1 to 3 carbon atoms, $R_2$ is an alkyl group of 1 to about 8 carbon atoms, a cycloalkyl group of 3 to about 7 carbon atoms or a phenyl group, and each $R_3$ independently is an alkyl group of 1 to 3 carbon atoms.

12. A compound according to claim 11 wherein the two $R_1$ groups together form a methylene group.

13. A compound according to claim 11 wherein $R_2$ is an alkyl group of 2 to about 5 carbon atoms.

14. A compound according to claim 13 wherein $R_2$ is an alkyl group of 3 or 4 carbon atoms.

15. A compound according to claim 14 wherein $R_2$ is n-propyl or n-butyl.

16. A compound according to claim 11 wherein each $R_3$ is a methyl group.

17. A salt according to claim 11 which is a halide salt.

18. A salt according to claim 17 in which the halide is a chloride or iodide salt.

19. The salt according to claim 11 wherein the two $R_1$ groups together form a methylene group, $R_2$ is n-propyl, each $R_3$ is methyl and the anion is a chloride ion, namely 2-propyl-5,6-methylenedioxyindane-1-dimethylammonium chloride.

20. The salt according to claim 11 wherein the two $R_1$ groups together form a methylene group, $R_2$ is n-butyl, each $R_3$ is methyl and the anion is an chloride ion, namely 2-butyl-5,6-methylenedioxyindane-1-dimethylammonium chloride.

21. A cis 2-alkyl-5,6-dialkoxyindane-1-trialkylammonium salt of Formula IVA

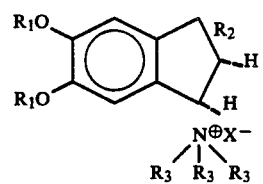

wherein the two $R_1$ groups together form an alkylene group of 1 to 3 carbon atoms, $R_2$ is an alkyl group of 1 to about 8 carbon atoms, a cycloalkyl group of 3 to about 7 carbon atoms or a phenyl group, each $R_3$ independently is an alkyl group of 1 to 3 carbon atoms and $X^-$ is an anion.

22. A salt according to claim 21 wherein the two $R_1$ groups together form a methylene group.

23. A salt according to claim 21 wherein $R_2$ is an alkyl group of 2 to about 5 carbon atoms.

24. A salt according to claim 23 wherein $R_2$ is an alkyl group of 3 or 4 carbon atoms.

25. A salt according to claim 24 wherein $R_2$ is n-propyl or n-butyl.

26. A salt according to claim 21 wherein each $R_3$ is a methyl group.

27. A salt according to claim 21 wherein $X^-$ is a halide ion.

28. A salt according to claim 27 wherein $X^-$ is a chlorine or iodide ion.

29. The salt according to claim 21 wherein the two $R_1$ groups together form a methylene group, $R_2$ is n-propyl, each $R_3$ is methyl and $X^-$ is a iodide ion, namely 2-propyl-5,6-methylenedioxyindane-1-trimethylammonium iodide.

30. The salt according to claim 21 wherein the two $R_1$ groups together form a methylene group, $R_2$ is n-butyl, each $R_3$ is methyl and $X^-$ is a iodide ion, namely 2-butyl-5,6-methylenedioxyindane-1-trimethylammonium iodide.

* * * * *